United States Patent [19]

Akopov et al.

[11] 4,378,901

[45] Apr. 5, 1983

[54] APPARATUS FOR APPLYING A STAPLE SUTURE

[76] Inventors: Ernest M. Akopov, Alexeevsky studentchesky gorodok, 6b proezd, dom 5a, kv. 28; July G. Shaposhinikov, ulitsa Chaikovskogo, 18, kv. 6, both of Moscow, U.S.S.R.

[21] Appl. No.: 153,625

[22] Filed: May 22, 1980

[51] Int. Cl.³ .............................................. B25C 5/00
[52] U.S. Cl. .................................... 227/19; 227/153; 227/DIG. 1
[58] Field of Search ................. 227/19, 155, 153, 152, 227/DIG. 1; 128/325, 334 R, 335

[56] References Cited

U.S. PATENT DOCUMENTS

| | | | |
|---|---|---|---|
| 3,315,863 | 4/1967 | O'Dea | 227/19 |
| 3,494,533 | 2/1970 | Green et al. | 227/DIG. 1 |
| 3,935,981 | 2/1976 | Akopov et al. | 227/19 |
| 3,949,923 | 4/1976 | Akopov et al. | 227/19 |
| 4,216,891 | 8/1980 | Behlke | 227/19 X |
| 4,227,638 | 10/1980 | Medina et al. | 227/155 |

Primary Examiner—John McQuade
Assistant Examiner—John S. Brown
Attorney, Agent, or Firm—Steinberg & Raskin

[57] ABSTRACT

The surgical instrument for applying a staple suture comprises a body with a split frame having a ∩-shaped member, whose one leg carries a die with a number of recesses. There is provided a detachable rod adapted to interlink the free ends of the legs of the ∩-shaped member, said rod having stops which embrace from outside the free ends of the legs of the ∩-shaped member so as to form, together with said free ends, a lock joint featuring a retainer of the rod position, said retainer being in fact a shoulder provided at the free end of each of said legs. The free ends of the legs are capable of moving towards each other due to resilience of the ∩-shaped member, the amount of the abovesaid travel of the free ends of the legs towards each other depending upon the size of the retaining shoulder, while the detachable rod and the free ends of the legs are adapted to enter each other along the legs so as to interact through the flat spots provided thereon. The instrument has also a die with the staple bending recesses, a staple head carrying a staple magazine and an ejector and being mounted slidably in the frame, as well as mechanical actuators of the staple head and ejector.

6 Claims, 9 Drawing Figures

APPARATUS FOR APPLYING A STAPLE SUTURE

FIELD OF THE INVENTION

The present invention relates to surgical instruments, viz., to instruments for applying staple sutures, and can be used in surgical practice for suturing the stomach, intestines, as well as for applying sutures in deep and narrow cavities, involving once-through application of relatively long staple sutures, and hence heavy loads on the stitching mechanism of the instrument within a very small extent of the operative wound.

BACKGROUND OF THE INVENTION

Known in the art are some surgical instruments for applying staple or multistaple sutures (cf., e.g., U.S. Pat. No. 3,315,863). These instruments include a frame shaped as a hook with a jaw carrying a die provided with recesses for the staples to bend, a staple head, a magazine with slots for staples, a staple ejector and mechanical actuators of the staple head and ejector. The instruments, however, are disadvantageous in having not adequately rigid construction of the frame shaped as a hook, which results in deformation of the hook and an inadmissible change in the magazine-to-die distance due to heavy loads imposed upon the instrument when applying lengthy multistaple sutures (which is the case when stitching up the stomach with a double-row suture 100 to 150 mm long). As a result, the proper mutual arrangement of the die recesses and the respective magazine slots is affected, whereby the staples fail to be bent tightly enough, the obtained suture is insufficiently hermetic, and hemostasis thus occurs. In order to increase rigidity of the frame and obtain a high-quality staunch suture, the cross-sectional dimensions of the frame elements are considerably increased, which adds to the weight of the instrument as a whole, a feature that affects adversely manipulations with the instrument within a restricted area of the operative field and the functional capabilities of the instrument, results in obtaining too a rough suture due to abnormally increased distance from the suture to the cut of the tissues.

The above-mentioned disadvantages are to a great extent eliminated in another instrument for suturing human organs, according to U.S. Pat. No. 3,494,533. Said instrument comprises a body with a closed rectangular frame adapted to interact with a staple head, comprising a staple magazine and an ejector, each of these having a mechanical actuator.

The frame consists of a ∩-shaped member one of whose legs carries a die, and a detachable rod, which interlinks the legs of the ∩-shaped member. The functional expediency of the construction of said instrument consists in that the closed frame may be opened aside of the die-carrying leg, whereby the instrument can be conveniently brought to the organ being sutured, e.g., in the case of the stomach resection.

Said instrument has a number of disadvantages, the principal of which is that the frame construction fails to provide an ample rigidity for the stitching mechanism which undergoes heavy loads applied in three mutually square directions when suturing tissues or organs. In addition, the frame of the instrument is too complicated, inconvenient and short-lived.

The above-mentioned disadvantages stem from the construction of the frame in the known instrument. Thus, the detachable rod of the frame is a cylinder-shaped, having a thread at one end and a head at the other. The rod is joined with the legs of the ∩-shaped member through a threaded hole in the die-carrying leg and through an additional intermediate sleeve having an external thread and adapted to be screwed into the threaded hole provided in the end of the other end of the ∩-shaped frame member. The detachable cylindrical rod is fitted in to the hole in the intermediate sleeve and screwed into the threaded hole in the die-carrying leg.

Inasmuch as the cylindrical rod serves also for locking in position the detachable staple magazine and and the discardable die, said rod runs through special centering holes in the magazine and die and hence has its cross-sectional diameter much less than the width of the magazine located in the staple head, and of the die. On the other hand, the cylindrical rod surface and the centering holes in the magazine and die should be accurately gauged to provide a required fitting accuracy, so that the thread on the rod end has still lesser diameter than the diameter of the rod gauged portion.

It is quite obvious that such a construction of the detachable rod, which is in fact one of the lateral sides of the closed frame, features much lower tensile rigidity and transverse rigidity in the plane of the frame and normally thereto than the rigidity of the other lateral side, which interlinks the legs of the ∩-shaped member as a permanent joint and which does not run through out the magazine and die. Besides, hinged joint of the cylindrical rod with the legs of the ∩-shaped frame member, the magazine and the die fails to compensate for twisting moments resulting from a transverse flexure of said components in the plane normal to the plane of the frame.

Great forces are applied to the stitching mechanism of the instrument in the course of compressing the tissues being sutured and performing a once-through deformation of a large number of staples; thus, for instance, the forces applied to the stitching mechanism when placing a double-row 100 to 150 mm long suture with staple made of a dia. 0.3 mm wire, amount to 100 or 140 kgf. It is due to low rigidity of the whole construction and on account of a hinged joint of the cylindrical rod with the legs of the ∩-shaped frame member, the magazine and the die, that the magazine-to-die clearance is increased in the direction of suturing, the magazine and the die are mutually dislodged in the plane of the frame and in a direction normal to the abovesaid plane. This leads to an axial misalignment of the staple recesses and the staple slots, an inadequately tight staple bending after the suturing and its distorted shape (asymmetrical bending) and hence to a nonstaunt suture, affected suture tightness and hemostasis.

Low rigidity of the detachable rod resulting from the frame construction, eventuates in an inadmissible deformation of the rod. As it is stated in the description of the instrument according to U.S. Pat. No. 3,494,533 (column 14, line 74), the rod must be discarded after use as having been subjected to bending forces and thus being liable to deform, thereby upsetting the central alignment of the magazine and die if reused. That is why the detachable cylindrical rod applied in said instrument is to be made discardable so that a fresh rod must be available for every next suturing operation, which is economically inexpedient.

Low durability of the cylindrical rod and its being unsuitable for multiple use is also due to the fact that small-diameter thread has to be made use of in the construction of the known instrument, which is subject to substantial wear and deformation upon multiple repeated screwing in and out, which is liable to cause abnormal plays in the threaded joint. In addition, such a rod is practically inapplicable in small-sized instruments adapted for use in, say, preschool children, since in this case the thread diameter should be still smaller and such a thread cannot be used a heavy-duty one.

In order to compensate for said disadvantages in the construction of the known instrument manifested themselves under heavy loads applied to the stitching mechanism thereof, one must increase the rigidity of the structural members of said mechanism by increasing the cross-sectional dimensions of the legs and of the lateral (with respect to the legs) side of the ∩-shaped frame member, as well as of the cylindrical rod. This, however, will render the instrument more bulky and will lead to a wider space between the suture staples and the cut of the tissues being sutured, performed along the leg of the ∩-shaped frame member, on account of which the obtained suture will be still more rough and be featured by a large tissue torus.

Complexity of the construction of the known instrument and its being inconvenient for use are accounted for by the fact that the detachable cylindrical rod of the frame must involve, for being linked to the free ends of the legs of the ∩-shaped member, one more intermediate piece made as a sleeve provided between the rod and one of the legs of the ∩-shaped frame member. Thus, the abovesaid sleeve is to be first made fast on the leg, than the cylindrical rod is to be fitted into a number of holes in the sleeve, magazine, die and die-carrying leg, which should be brought in strict register with one another. This done, one must give the rod several turns. The rod end has a tapered surface which, when the rod is being set to working position, presses as a cam upon a special projection in the centring hole of the magazine and upon the cylindrical face of the hole in the die.

One more inconvenient feature of the known instrument resides also in the fact that the magazine and die can be replaced not until the cylindrical rod is taken apart and completely removed from the instrument, and the instrument itself is taken out of the operative wound. The instrument cannot be applied repeatedly unless a new set of magazine, die and rod is available and these components are set to their respective working position. This place a limitation upon the functional capabilities of the instrument, in particular, prevents its convenient use, without removing the instrument from the operative wound, for applying two parallel sutures to the organ, accompanied by severing the tissues between the sutures with a scalpel, which proves to be expedient when applying sutures to the remaining stump of the organ operated upon, and to its ablated portion, e.g., when stitching up the stomach, or for establishing a tube from the walls of the greater curvature of the stomach in the case of esophagoplasty.

In addition, the intermediate sleeve and small-diameter threaded hole in the leg of the ∩-shaped frame member are inconvenient cleansing.

OBJECTS OF THE INVENTION

A primary and essential object of the present invention is to provide a surgical instrument for applying a staple suture, wherein the construction of the body split frame would have an increased rigidity to a maximum extent approximating the rigidity of the solid frame due to a higher constructional rigidity of the detachable rod of the frame and due to the provision of such a joint of said rod with the ∩-shaped frame member that would compensate for twisting moments liable to result from the effect of transverse loads upon the leg carrying the die.

Another object of the present invention is to provide a surgical instrument that enables a better quality of the suture applied.

Still another object of the present invention is to extend the functional capabilities of the instrument and impart higher maneuvrability thereto and at the same time to reduce the cross-sectional dimensions of the frame sides.

Still more object of the present invention is to prolong the service life of the proposed instrument for applying a staple suture.

Yet still more object of the present invention is to render the instrument more convenient in operation and to simplify the construction thereof.

One more object of the present invention is to cut down the time for the instrument to get ready for operation.

The aforesaid and other objects are accomplished due to the fact that in a surgical instrument for applying staple sutures, comprising a body with a split frame having a ∩-shaped member, one of whose legs carries a die with recesses and a detachable rod adapted to interlink the free ends of the legs of the ∩-shaped member, a staple head having a staple magazine and an ejector and slidably mounted in the frame, and mechanical actuators of the staple head and the staple ejector, according to the present invention, the detachable rod has stops which embrace from outside the free ends of the legs of the ∩-shaped member so as to form together therewith a lock joint, featuring a retainer of the rod position made as a shoulder provided at the free end of each leg, said free ends of said legs being adapted to move towards each other due to resilience of the ∩-shaped member, over a length depending upon the size of the retaining shoulder, while the detachable rod and the free ends of the legs are engageable by entering each other along the legs to interact through flat spots provided thereon.

Such a construction of the split frame makes it possible to increase the rigidity of the detachable rod in three mutually perpendicular directions and the rigidity of the joint of the rod with the legs of the ∩-shaped frame member. A lock joint of the detachable rod with the legs practically rules out any mutual displacement of these under the action of loads imposed upon the frame in the course of suturing, including a turn of the free ends of the legs with respect to the detachable rod in the plane normal to the plane of the frame, whereas said turn take place in the known instrument. Thanks to this the instrument components are less liable to deform under otherwise equal conditions, and more favourable conditions are established for retention of a proper mutual arrangement of the magazine slots and the die recesses, while under the action of compression forces of the organs and of the forces of staple deformation during the suturing. This in turn conduces to a higher-quality forming of the suture stitches, adds to the suture tightness and hence to its staunchness and provides for better hemostasis.

Increase of rigidity of the construction makes it possible to reduce the width of the stitching mechanism of the instrument in order to provide closer space between the suture stitches and the cut of tissues performed along the frame leg carrying the die, whereby a more "delicate" suture can be obtained. On other hand, a possibility is provided to increase overall loads imposed upon the instrument without increasing the cross-sectional dimensions of the frame and the stitching mechanism of the instrument, so as to apply sutures of much greater length, incorporating a greater number of staples to be bent at once.

Thus, the construction of the present invention makes it possible to provide such instruments as, say, for stitching up the stomach with a double-row suture 100 to 150 mm long, using staples made of a dia. 0.3 mm wire, or for suturing relatively stiff and massive muscular tissues with staples featuring comparatively larger cross-sectional dimension of the wire they are made of, e.g., 0.4 mm and over.

A possibility of reducing the cross-sectional dimension of the frame components, i.e., the legs of the ∩-shaped member and the frame side lateral with respect to said legs, renders the instrument more manoeuvrable and reduces its weight. Therefore the construction of the present invention is expedient to use also in the instruments for applying staple sutures in deep narrow cavities, in the instruments intended for use in pediatric surgery under conditions of closely bounded size of the operative wound, especially for surgery in preschool children, and in the instruments intended for stitching up organs deficient in sound tissues that would be employed for setting the working portion of the instrument to the suturing position, say, in the case of suturing the duodenum for peptic ulcer, or suturing the pharynx for carcinoma, where every saved millimeter of tissue required for setting the instrument working portion to the suturing position, is of paramount importance and is a decisive factor for applicability of the instrument for a given operation.

Considerable increase in the rigidity of the detachable red of the frame rules out any possibility of its inadmissible deformation and its being made discardable. Practical durability of the detachable rod becomes unlimited, which in turn adds to the service life of the instrument as a whole.

The distinguishing constructional features of the instrument proposed in the present invention make it possible to provide a detachable rod linked directly to the legs of the ∩-shaped member and therefore involving no additional intermediate piece to be inserted between the rod and the ∩-shaped member, as is the case with the known instrument. Thanks to this the construction of the frame composed only of two members, become simpler and more technologically practicable as ensuring more convenient disassembly and reassembly of the instrument.

It is desirable that the free ends of each leg of the -shaped member have slots, which open towards the end faces of the legs, the side faces of the slots have retaining shoulders, and the rod has depressions on the area that enters the slot in the corresponding leg.

Such a constructional arrangement provides for convenience in cleansing and washing the frame components devoid of any narrow-space enclosed hollows or small-diameter threaded holes.

Another embodiment of the instrument frame is also practicable, wherein the detachable rod is expedient to have openings with flat faces, which openings are situated within the area of the rod to be engaged with the free ends of the legs provided with the retaining shoulder.

The outer surfaces of the free ends of the legs may have cut outs forming a shoulder.

It is expedient that the retaining shoulder of the free end of one leg and the stops of the detachable rod have bevelled edges situated on their surfaces adapted to interact when the rod is being fitted in position. This attains an automatic approximation of the free ends of the legs of the ∩-shaped frame member and provides convenience in setting the detachable rod to working position.

It is favourable that one of the rod ends has an oblong portion forming a handle, while the rod end has a flange adapted to enter the cutout in the free end of the die-carrying leg.

PREFERABLE EMBODIMENTS OF THE INVENTIONS

The instrument comprises a body 1 (FIG. 1) with a closed rectangular frame 2, which consists of a ∩-shaped member 3 (FIGS. 1, 2) having legs 4, 5 whose free ends are interlinked by a detachable rod 6. The leg 4 carries a die 7 having recesses for staple to bend. A staple head 8 (FIG. 1) is adapted to interact with the frame 2 and has a stem 9 accommodated in a slot 10 made in the body 1.

The staple head 8 has lugs 11 (FIG. 3) engaged with sides 6 and 12 of the frame, which are lateral with respect to the die 7 (FIG. 1) (as the detachable rod 6 serves in fact as a lateral side for the frame 2, therefore Ref. No. 6 will hereinafter designate both the detachable rod and the lateral side of the frame 2). The lateral sides 6 and 12 restrict mutual displacement of the staple head 8 and the frame 2 in the plane of the latter and in the direction normal to the plane of the frame 2. The stem 9 has projections 13 and 14 which, when in working position, are accomodated in longitudinal grooves 15 and 16 made in the body 1.

The staple head 8 comprises a staple magazine 17 (FIG. 4) with slots 18, and an ejector 19 with lamels 20 corresponding to the slots in the magazine 18. The ejector 19 has a stem 21 accomodated in a slot 10 of the body 1 under the stem 9 of the staple head. The magazine 17 and the ejector 19 are held to the staple head through a detachable cover 22, which is slidable with respect to the magazine 17 in the direction away from the die 7 for a length exceeding the height of the magazine 17. Thanks to this the magazine 17 can be released after the suturing and disengaged from the staple head 8 by a force applied thereto in a direction perpendicular to the plane of the frame 2, and a change magazine loaded with staples can be fitted instead.

Figure 4:
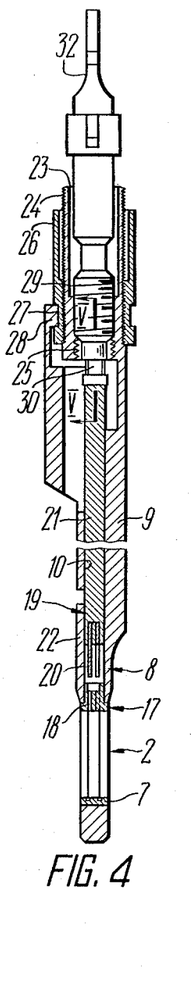
FIG. 4 is a section taken along the line IV—IV in FIG. 1.

The stem 9 of the staple head is provided with a hollow tailpiece 23 having an external thread 24 and an internal thread 25. A nut 26 is engaged with the external thread 24, which is in fact a mechanical actuator of the staple head 8, and imparts translational motion (advancement) to the staple head 8 with the magazine 17 with respect to the die 7 when setting the suturing gap. The nut 26 is locked on the body 1 against longitudinal displacement by means of an annular groove 27 adapted to interact with a projection 28 on the body 1.

Figures 5, 6:
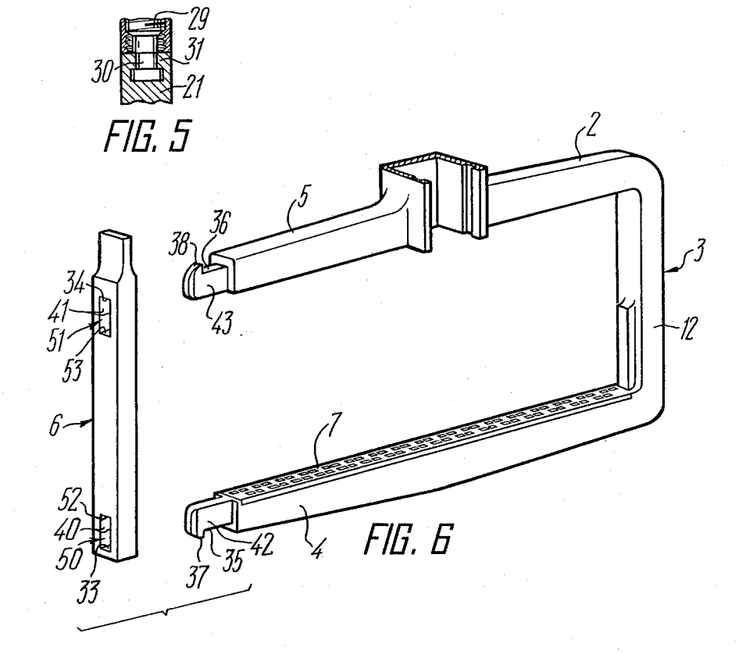
FIG. 5 is a section taken along the line V—V in FIG. 4.
FIG. 6 is a perspective separate view of another embodiment of the frame when set apart, according to the present invention.

Engaged with the internal thread 25 of the tailpiece 23 is a screw 29, which is in fact a mechanical actuator of the ejector 19 imparting translational motion (advancement) to the latter with respect to the magazine 17 and the die 7, required for the staples to bend to form a suture. The screw 29 has an annular groove 30 with which the stem 21 of the ejector 19 is engaged through a fork 31 (FIG. 5) provided at its end, and is provided with a removable handle 32.

The detachable rod 6 (FIG. 1) of the frame 2 has stops 33, 34 (FIGS. 2, 6) which embrace outer surfaces 35 and 36 of the free ends of the legs 4 and 5 of the ∩-shaped frame member 3. This prevents the free ends of the legs 4 and 5 from moving apart in the direction of suturing and hence rules out any change in the suturing gap defined between the die 7 (FIG. 1) and the magazine 17, which are liable to occur under the action of the load from compressing the organs being sutured and from a once-through bending of a great number of staples when suturing.

The detachable rod 6 (FIGS. 2, 6) with the stops 33, 34 forms, together with the free ends of the legs 4, 5 of the ∩-shaped member 3 a lock joint, comprising retainers of the rod position, which are in effect a shoulder 37, 38 at the free end of each leg 4, 5. The shoulders 37, 38 retain the rod 6 from displacing along the legs 4, 5 and against an occasional disengaging from the ∩-shaped member 3 of the frame 2.

Figure 7:
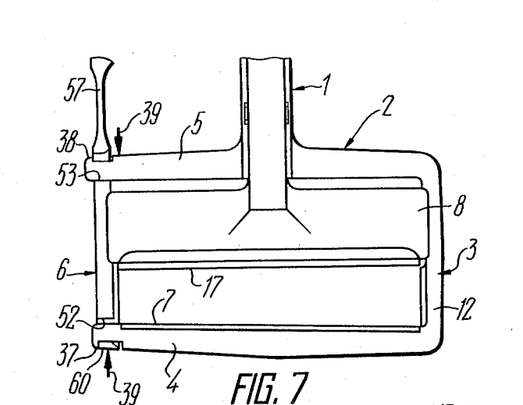
FIG. 7 shows a mutual arrangement of the legs of the ∩-shaped frame member before removing the rod.

With a view to providing a possibility to open the frame aside of the die 7 for convenient approaching of the instrument to the organ being sutured, and then to lock the legs 4, 5 after placing the organ to the suturing position, the free ends of the legs 4, 5 are traversable towards each other within the limits of resilience possessed by the ∩-shaped member 3 of the frame 2 for a length equal to or in excess of the height of the retaining shoulder, say, 38. Owing to this when the surgeon presses the ends of the legs 4, 5 towards each other with the fingers of his hand in the direction facing arrows 39 (FIG. 7) the detachable rod 6 gets out of engagement with the retaining shoulder 38. It is due to such a constructional feature of the frame 2 that the rod 6 can be removed momentarily in a single motion.

Figures 8, 9:
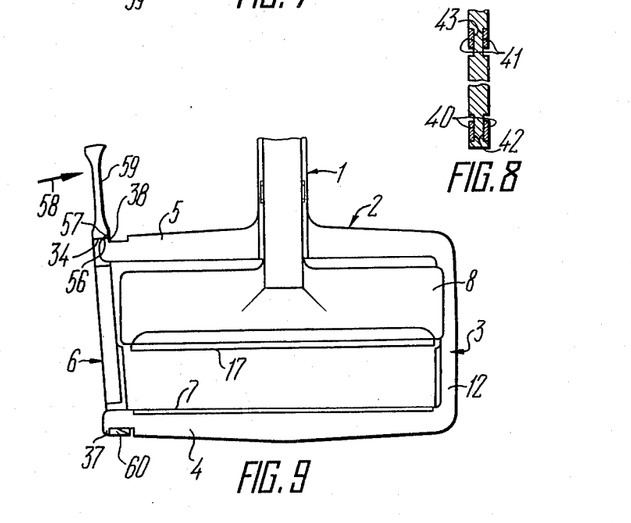
FIG. 8 is a section taken along the line VIII—VIII in FIG. 1.
FIG. 9 shows the frame when the detachable rod is being fitted onto the legs of the ∩-shaped member.

The detachable rod 6 and the free ends of the legs 4, 5 of the ∩-shaped member 3 are so arranged constructionally as to enter each other along the legs 4, 5 and to interact with flat spots 40, 41 (FIGS. 2, 6, 8) provided on the rod 6, and flat spots 42, 43 provided on the free ends of the legs 4, 5.

In one of the embodiments of the instrument the flat spots 42, 43 (FIG. 2) on the free ends of the legs 4, 5 of the ∩-shaped member 3 are in effect the walls of slots 44, 45, which open towards end faces 46, 47 of the legs. The retaining shoulders 37, 38 in this case are located on side faces of the slots 44, 45, while the flat spots 40, 41 on the rod 6 are in fact the bottoms of depressions 48, 49 on the surface of the rod 6 within the area of its engagement into the slots 44, 45 of the legs 4, 5 of the U-shaped member 3.

In another embodiment of the instrument the flat spots 40, 41 (FIG. 6) are essentially the faces of through openings 50, 51 made in the detachable rod 6 within the areas of fitting the rod 6 onto the free ends of the respective legs 4, 5 provided with the retaining shoulders 37, 38.

A system of the mutually associated flat spots 40, 41 on the detachable rod 6 and flat spots 42, 43 on the free ends of the legs 4, 5 of the ∩-shaped member 3 of the frame 2 provides for a reliable locking of the legs with respect to each other in the plane normal to the plane of the frame, and precludes any turning of the legs 4, 5 with respect to the rod 6 under the action of transverse loads upon the legs, which is the case with the known instrument, where said components are hinge-joined.

The adopted construction of the detachable rod 6 and the legs 4, 5 of the ∩-shaped member 3 imparts high rigidity to the frame 2 to a maximum extent approximating that of a construction featuring permanent joint of the arms of a rectangular frame. Thanks to this constructional feature there is attained a stable mutual arrangement of the recesses in the die 7 and the staple slots in the magazine 17 in the course of suturing and hence a closer spacing of the suture stitches, hermetic union and perfect hemostatic effect of the suture obtained. Higher rigidity of the construction enables a considerable reduction in the cross-sectional dimension of the stitching mechanism under otherwise identical conditions.

For fear least any residual strain should be experienced by the ∩-shaped member 3 of the frame 2 due to overpressing when bringing the ends of he legs 4, 5 together in order to remove the rod 6, the latter has restrictive areas 52, 53 (FIGS. 7, 2, 6), which rule out any possibility for the free ends of the legs 4, 5 to be brought together beyond the limit of resilience of the ∩-shaped member 3 of the frame 2.

The stops 33, 34 (FIG. 2) of the detachable rod 6, which embrace the legs 4, 5 of the ∩-shaped member 3 of the frame 2, and the areas 52, 53 restricting the amount of travel of the ends of the legs 4, 5 towards each other, are in fact the faces of the exposed depressions 48, 49 in the former embodiment of the instrument, and the faces of the through openings 50, 51 (FIG. 6) in the latter embodiment. This feature imparts constructional and technological simplicity to the frame 2 and its components and provides for convenience in cleansing and washing the frame components devoid of any narrow-space enclosed hollows or slots.

A possibility of joining the rod 6 (FIG. 9) with the legs 4, 5 of the ∩-shaped member 3 of the frame 2 and with the staple head 2 aside of the die 7 and the staple head 8 rather than on top as is the case with the known instrument disclosed in by U.S. Pat. No. 3,494,533, enables the rod 6 to be made as a bar whose shape and cross section on the section confined within the legs 4, 5 of the ∩-shaped member 3 of the frame 2, correspond to the side 12 of the frame made integral with the legs 4, 5. Thus, there is attained practically equal deformation resistance of the detachable rod 6 (FIG. 1), which serves as one of the sides of the frame 2, and of the other side 12 of the frame 2, inadmissible deformation of the rod 6 and its replacement with a new rod after every suturing are ruled out.

The detachable rod 6 of the frame 2, unlike the prototype construction, is not engaged with the die 7 and the magazine 17, which enables the magazine 17 to be replaced immediately in the operative wound without preliminarily removing the rod 6 and taking the instrument out of the operative wound. This provides for convenience when applying two parallel sutures, followed by severing the tissues between the sutures with a scalpel, which is the case with, say, resection of the stomach with applying a suture to the gastric stump and to the ablated portion of the stomach, or when establishing a tube from the walls of the greater curvature of the stomach in the case of esophagoplasty.

The cross-sectional dimensions of the legs 4, 5 (FIG. 1) of the frame 2 are selected proceeding from their rigidity to transverse flexure high enough to ensure the stability of clearances between the die 7 and the magazine 17 throughout their length during compressing and suturing of the organ. Therefore it is expedient that a possibility for the free ends of the legs 4, 5 to approximate each other within the limit of resilience possessed by the ∩-shaped member 3 of the frame 2 be provided due to springiness of the frame lateral side 12. With a relatively great length of the legs 4, 5 of the frame 2 (which amounts to 100 or 150 mm in the instrument for suturing the stomach) and small transverse flexure of the side 12 within the limit of resilience, one can obtain a required amount of approximation of the free ends of the legs 4, 5 (i.e., by 1 or 2 mm) and select a corresponding height of the retaining shoulders 37, 38 large enough for reliably locking the detachable rod 6 of the frame 2 in working position. The cross-sectional dimensions of the frame sides 6 and 12 may be reduced considerably but so as to provide an adequate resistance to tension under the loads imposed upon the frame 2.

The cutouts 54, 55 are provided on the outer surface of the free ends of the legs 4, 5 to establish the retaining shoulders 37, 38. The retaining shoulder 38 (FIG. 9) of the free end of the leg 5 of the ∩-shaped member 3 has a bevelled edge 56, while the stops 34 of the detachable rod 6 have bevelled edges 57 situated within the areas of their interaction when the rod 6 is being set to working position. The bevelled edges 56, 57 make it possible, after the rod 6 has been engaged with the retaining shoulder 37 on the leg 4, to automatically approximate the free ends of the legs 4, 5 with the rod 6 rotating in the direction of an arrow 58, and to lock the rod 6 by the retaining shoulder 38 by virtue of the elastic forces of the springy ∩-shaped member 3. Such a constructional arrangement to a maximum extent simplifies assembling of the frame 2 and engaging of the rod 6 with the legs 4, 5 of the ∩-shaped frame member 3 after the organ being sutured has been placed between the die 7 and the magazine 17.

To provide convenience in handling the detachable rod 6 (FIG. 1) when assembling or disassembling the frame 2, the rod 6 has an oblong handle 59 at one of its ends, and a flange 60 at the other end, said flange being adapted to enter the cutout 54 at the free end of the leg 4, which carries the die 7, so as not to go beyond the outline of the leg 4.

The frame sides 6 and 12 have cutouts 61 to provide convenience if disengaging the staple head 8 from the frame 2, or their assembling without preliminarily removing the rod 6.

The instrument of the present invention operates as follows.

Before operation the ejector 19 (FIG. 4) is set to its rearmost position, and the magazine 7 loaded with staples (not shown) is held to the staple head 8. The rod 6 of the frame 2 (FIG. 1) and the handle 32 of the screw 29 are out of position on the instrument. The staple head 8 is set to the initial position, after having been withdrawn to the rearmost position, whereupon the nut 26 is given a turn to engage the lugs 11 (FIG. 3) of the staple head 8 with the side 12 of the frame 2.

Figure 1:
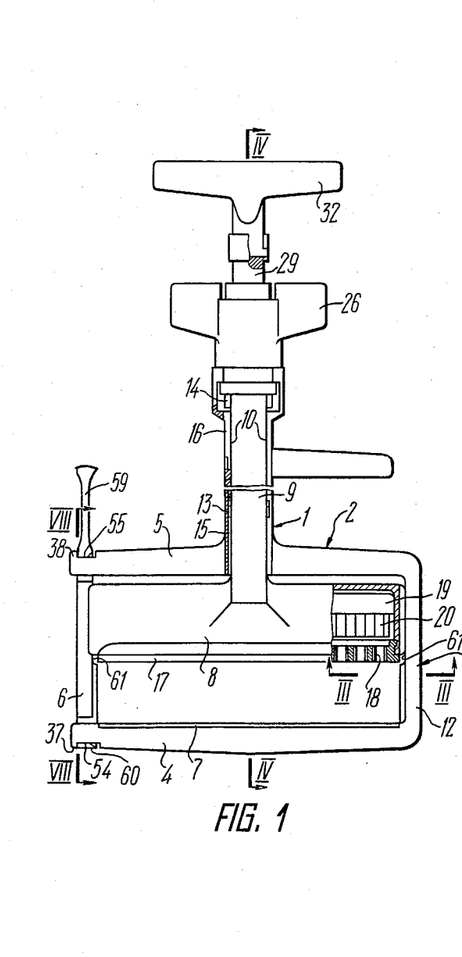
FIG. 1 is a surgical instrument for applying a staple suture in a general partly cutaway view, according to the present invention.
Figures 2, 3:
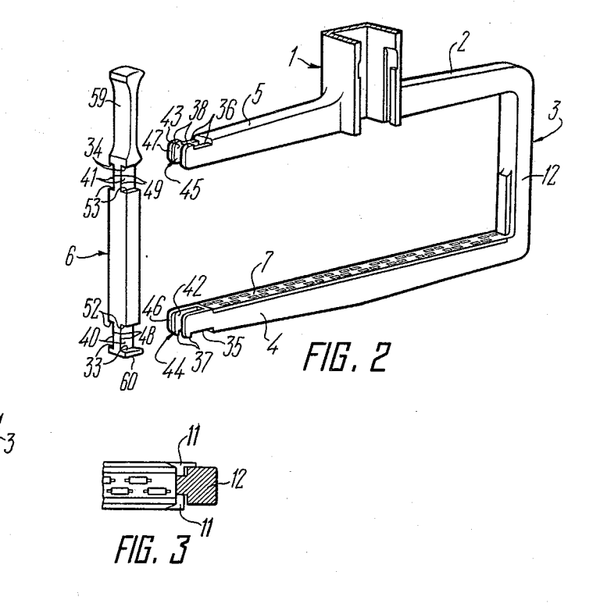
FIG. 2 is a perspective separate view of a frame in the instrument of FIG. 1 when taken apart, according to the present invention.
FIG. 3 is a scaled-up sectional view of FIG. 1, taken along the line III—III therein.

After having prepared the organ to be sutured according to conventional routine procedure, e.g., the stomach for resection, one must bring the leg 4 (FIG. 9) under the organ being sutured so as to place the organ between the die 7 and the magazine 17. Then taking hold of the handle 59 one must fit the bottom end of the detachable rod 6 into the slot 44 (FIG. 2) in the leg 4 so as to engage the flange 60 (FIG. 9) with the retaining shoulders 37, whereupon the rod 6 is turned till meeting the stop. As a result, the bevelled edges 57 of the stops 34 of the rod 6 interact with the bevelled edges 56 of the retaining shoulders 38 on the free end of the leg 5, thus approximating said end to the free end of the leg 4 and exerting an elastic strain upon the ∩-shaped member 3 of the frame 2. Once the stops 34 have passed over the shoulders 38 the legs 4, 5 are returned into the initial position by virtue of elastic forces, thus automatically locking the rod with the retaining shoulders 38 (FIG. 1).

Then the frame 2 is positioned correspondingly to the place of suture application, and the walls of the organ are compressed between the die 7 and the magazine 17 by rotating the nut 26 so as to set the suturing gap required.

Next the handle 32 is engaged with the screw 29 and the latter is rotated so as to expel the staples from the magazine 17 by virtue of the ejector 19 (FIG. 4). Upon being driven out of the magazine the staples pierce the walls of the organ, enter into the recesses of the die 7 and become bent to form a suture.

After the ablated portion of the organ has been severed along the leg 4 (FIG. 1), one must rotate the nut 26 so as to bring the die 7 somewhat apart from the magazine 17, thus releasing the sutured organ.

To remove the rod 6 (FIG. 7) of the frame 2 one must place the middle finger upon the free end of the leg 4 nearby the flange 60 of the rod 6 and the thumb upon the leg 5 so as to touch the handle 59 of the rod 6. Then one must press the legs 4 and 5 towards each other in the direction facing the arrows 39 to disengage the rod 6 with the retaining shoulders 38 of the leg 5 and to turn the latter with respect to the retaining shoulders 37 of the leg 4. Next, taking hold of the handle 59 one must remove the rod 6 from the ∩-shaped member 3 of the frame 2.

When applying two parallel sutures to an organ, followed by severing the tissues between the sutures applied, which is the case with say, resection of the stomach involving application of a staple suture both to the gastric stump and to the ablated portion of the stomach, one must apply first one suture as it has been described hereinbefore. Once the walls of the organ has been sutured, one must rotate the nut 26 to retract the staple head 8 (FIG. 1) together with the magazine 17 into the initial position, thus relieving the walls of the organ from compression. Then the cover 22 (FIG. 4) is shifted in the direction opposite to the die 7, thus disengaging the magazine 17. Then a fresh magazine 17 loaded with staples is put into the staple head 8 and held in position by the cover 22. Replacement of the empty magazine 17 by a loaded one, after having applied the first suture, is carried out without removing the rod 6 from the ⋂-shaped member 3 of the frame 2, without bringing the leg 4 with the die 7 from under the sutured organ and without taking the instrument out of the operative wound.

To apply a second suture one must shift the frame 2 a distance of from 3 to 4 mm with respect to the line of staples of the first suture, compress the walls of the organ between the die 7 and the magazine 17 and apply the other suture, while manipulating the instrument and its components as in application of the first suture. Then one must sever the walls of the sutured organ between the first suture and the stitching mechanism, by a scalpel along the leg 4. Then the magazine 17 is withdrawn a little from the die 7 to release the part of the organ stitched by the second suture.

What we claim is:

1. A surgical instrument for applying a staple suture comprising:

a body constituted by a substantially ⋂-shaped frame having a side and a pair of legs extending therefrom, said legs having respective free ends which are capable of moving toward each other due to resilience of said ⋂-shaped frame;

a rod detachably carried by said free ends of said legs at respective areas of interaction to impart rigidity to said frame, said rod being formed with a pair of inwardly facing stop surfaces, each of which embraces an outwardly facing surface formed on a respective one of said free ends so as to define a lock joint therewith;

retaining means formed on said free ends for fixing said rod in position when said lock joint is defined, said retaining means including a retainer shoulder formed on each of said free ends, each shoulder extending outwardly beyond a respective one of said outwardly facing surfaces formed on said free ends, and wherein the extent of movement of said free ends toward each other is determined by the size of said retainer shoulders;

said rod and said free ends of the frame legs being formed with respective flat spots at said areas of interaction, said flat spots being located in planes which are substantially parallel to the plane on which said frame is situated, said flat spots formed on said rod being contiguous with said flat spots formed on said free ends;

one of said legs and said rod being receivable within the other of said free legs and said rod in the direction defined by said legs;

a die having recesses formed therein mounted on one of said legs;

a staple head carrying a staple magazine slidably mounted in said frame;

ejection means mounted on said frame for driving staples from said magazine;

means for actuating said staple head; and means for actuating said ejection means.

2. A surgical instrument as claimed in claim 1, wherein a slot is formed in the free end of each leg of the ⋂-shaped frame, which slots open toward the end faces of the legs, while the side faces of the slots have said retaining shoulders formed therewith, and wherein the rod has depressions formed in the areas of interaction which are received within the slot in the corresponding leg.

3. A surgical instrument as claimed in claim 1, wherein the rod has openings formed therein defining said flat faces, said openings being situated within the areas of said rod which are to be engaged with the free ends of the respective legs provided with the retaining shoulders.

4. A surgical instrument as claimed in claim 1, wherein cutouts are formed on the outer surface of the free ends of the legs to form the retaining shoulders.

5. A surgical instrument as claimed in claim 4, wherein one of the ends of said rod is shaped as an oblong extension that forms a handle, and wherein the other end of the rod has a flange adapted to enter the cutout provided at the free end of the leg carrying said die so as to be arranged within said cutout.

6. A surgical instrument as claimed in claim 1, wherein the retaining shoulder at the free end of one of the legs and the stop surfaces of the detachable rod have bevelled edges situated on the surfaces which are adapted to interact when the rod is being fitted in position.

* * * * *